US011912906B2

(12) United States Patent
Stafeil et al.

(10) Patent No.: US 11,912,906 B2
(45) Date of Patent: Feb. 27, 2024

(54) HOT MELT ADHESIVE CONTAINING A HYDROGENATED STYRENIC BLOCK COPOLYMER AND AN ETHYLENE VINYL ACETATE COPOLYMER EXHIBITING LOW BLOCKING FORCE

(71) Applicant: Bostik, Inc., Wauwatosa, WI (US)

(72) Inventors: Kevin Stafeil, Delafield, WI (US); Kathleen M Farris, West Allis, WI (US)

(73) Assignee: Bostik, Inc., Wauwatosa, WI (US)

( * ) Notice: Subject to any disclaimer, the term of this patent is extended or adjusted under 35 U.S.C. 154(b) by 935 days.

(21) Appl. No.: 14/329,058

(22) Filed: Jul. 11, 2014

(65) Prior Publication Data

US 2015/0017868 A1    Jan. 15, 2015

Related U.S. Application Data

(60) Provisional application No. 61/957,778, filed on Jul. 11, 2013.

(51) Int. Cl.

| | |
|---|---|
| *C09J 157/02* | (2006.01) |
| *A61L 15/24* | (2006.01) |
| *A61L 15/58* | (2006.01) |
| *B32B 5/02* | (2006.01) |
| *B32B 5/26* | (2006.01) |
| *B32B 7/12* | (2006.01) |
| *B32B 37/12* | (2006.01) |
| *C08L 23/08* | (2006.01) |
| *C08L 53/02* | (2006.01) |
| *C08L 91/00* | (2006.01) |
| *C09J 11/08* | (2006.01) |
| *C09J 123/08* | (2006.01) |
| *C09J 153/02* | (2006.01) |

(52) U.S. Cl.
CPC ............ *C09J 157/02* (2013.01); *A61L 15/24* (2013.01); *A61L 15/585* (2013.01); *B32B 5/022* (2013.01); *B32B 5/26* (2013.01); *B32B 7/12* (2013.01); *B32B 37/1207* (2013.01); *B32B 37/1292* (2013.01); *C08L 23/0853* (2013.01); *C08L 53/02* (2013.01); *C08L 91/00* (2013.01); *C09J 11/08* (2013.01); *C09J 123/0853* (2013.01); *C09J 153/02* (2013.01); *B32B 2037/1215* (2013.01); *B32B 2250/02* (2013.01); *B32B 2250/20* (2013.01); *B32B 2255/02* (2013.01); *B32B 2255/26* (2013.01); *B32B 2405/00* (2013.01); *B32B 2439/00* (2013.01); *B32B 2519/00* (2013.01); *B32B 2535/00* (2013.01); *B32B 2555/02* (2013.01); *C09J 2301/304* (2020.08); *Y02P 20/582* (2015.11); *Y10T 428/2891* (2015.01); *Y10T 442/60* (2015.04); *Y10T 442/659* (2015.04); *Y10T 442/674* (2015.04)

(58) Field of Classification Search
CPC ........ C09J 157/02; B32B 5/022; A61F 15/24; A61F 15/585
See application file for complete search history.

(56) References Cited

U.S. PATENT DOCUMENTS

| | | | | |
|---|---|---|---|---|
| 4,052,368 | A * | 10/1977 | Larson | C08G 63/688 528/293 |
| 4,712,808 | A * | 12/1987 | Beh-Forrest | B42C 9/00 281/15.1 |
| 5,559,165 | A | 9/1996 | Paul | |
| 6,143,818 | A * | 11/2000 | Wang | C08K 5/01 524/528 |
| 7,442,739 | B1 * | 10/2008 | Hatfield | C09J 153/02 524/474 |
| 2002/0022425 | A1 * | 2/2002 | Tsurumaki | D03D 27/00 442/352 |
| 2004/0115456 | A1 * | 6/2004 | Kanderski | C09J 123/142 428/500 |
| 2006/0135694 | A1 * | 6/2006 | Vaughan | C09J 123/0853 525/88 |
| 2011/0021103 | A1 * | 1/2011 | Alper | B32B 5/26 442/329 |
| 2013/0090421 | A1 * | 4/2013 | Vitrano | C09J 123/0853 524/505 |

FOREIGN PATENT DOCUMENTS

| | | |
|---|---|---|
| JP | 2010-077372 | 4/2010 |
| JP | 2011-236379 | 11/2011 |
| WO | WO 2005/014673 A1 | 2/2005 |

OTHER PUBLICATIONS

Hermel, T. J., et al., Role of Molecular Architecture in Mechanical Failure of Glassy/Semicrystalline Block Copolymers: CEC vs. CECEC Lamellae, Macromolecules, 2003, 36, 2190-2193.*
Kraton G1652 E Polymer Data Document May 13, 2011 (Year: 2011).*
Larrañaga, Michael D. et al. "Hawley's Condensed Chemical Dictionary", John Wiley & Sons, Incorporated, Sixteenth edition, pp. 1051, 1425-1426. (Year: 2016).*
The International Search Report dated Oct. 22, 2014 of the International Searching Authority in corresponding PCT International Application No. PCT/US2014/046283.

(Continued)

*Primary Examiner* — Peter Y Choi
(74) *Attorney, Agent, or Firm* — Christopher R. Lewis

(57) ABSTRACT

A hot melt adhesive composed of an ethylene vinyl acetate copolymer, a hydrogenated styrenic block copolymer, a tackifying resin, and a liquid plasticizer. The preferred ethylene vinyl acetate copolymer has a vinyl acetate content between 8 and 28 percent by weight, and the preferred hydrogenated styrenic block copolymer is a styrene-ethylene-butylene-styrene having about 30% styrene content and essentially no diblock. The hot melt gives excellent peel strength when used as a construction adhesive for disposable nonwoven articles. It can also be formulated to exhibit very low bleed through and blocking characteristics when used on low basis weight nonwoven fabrics.

23 Claims, No Drawings

(56) References Cited

OTHER PUBLICATIONS

The Written Opinion dated Oct. 22, 2014 of the International Searching Authority in corresponding PCT International Application No. PCT/US2014/046283.
The International Preliminary Report on Patentability dated Jan. 21, 2016 of the International Bureau of WIPO in corresponding PCT International Application No. PCT/US2014/046283.

* cited by examiner

HOT MELT ADHESIVE CONTAINING A HYDROGENATED STYRENIC BLOCK COPOLYMER AND AN ETHYLENE VINYL ACETATE COPOLYMER EXHIBITING LOW BLOCKING FORCE

BACKGROUND OF THE INVENTION

The present invention relates to hot melt adhesives, and more specifically to a hot melt adhesive that is composed of an ethylene vinyl acetate copolymer, a hydrogenated styrenic block copolymer, a tackifying resin, and a liquid plasticizer.

Historically, adhesive formulators have struggled to impart low viscosity, fast set speed, superior adhesion, and reduced cold flow and/or blocking to their products. Many of these properties are mutually exclusive using conventional raw materials and formulation techniques. This invention details a novel way a hot melt formulator can impart low viscosity, fast set speed, superior adhesion, and reduced cold flow and/or blocking to their products without compromising other properties.

Adhesives used to laminate thin and/or porous substrates such as nonwovens used in the construction of disposable diapers cannot exhibit cold flow, blocking, or migration. Traditional ethylene/vinyl acetate copolymers (EVA), amorphous polyalpha-olefins (APAO) and styrenic block copolymer (SBC) based adhesives used to laminate or bond thin and/or porous substrates typically struggle with the balance of reducing cold flow, migration, and/or blocking, while increasing adhesion properties.

Adhesives used in applications in which substrates are laminated, are often required to adhere to a wide variety of surface characteristics (treatments, recycled content, porosity). The substrates themselves can also vary in physical characteristics, such as rigidity, density, and chemical make-up. As a result, adhesives must be formulated to overcome these obstacles. Consequently, adhesive formulators are continuously evaluating new materials and novel formulation strategies in order to develop an adhesive with the broadest possible application window. An adhesive's application window can be defined as an adhesive's ability to overcome an application's deficiencies and/or manufacturing variables. The current invention details a novel way a hot melt formulator can maximize properties beneficial to lamination applications.

Historically, adhesive formulators have had to balance fast set speed with adhesion. Faster setting adhesives typically have poorer adhesion. Increasing the adhesion properties of a traditionally formulated low viscosity adhesive will also cause that adhesive to exhibit more cold flow and/or blocking. Cold flow can be defined as the tendency of the adhesive to flow or "creep" under low pressure at relatively low temperatures. Blocking is defined as the undesired adhesion of a coated adhesive to substrates it comes into contact with during shipping and/or storage. This is particularly problematic when dealing with very porous substrates, such as nonwoven fabrics.

Over the years, adhesive formulators have utilized a variety of different polymers as well as other additives in their formulations to obtain a balance of these attributes. These polymers include, but are not limited to, polyolefins (ethylene- or propene-based polymers), styrenic-based copolymers (both saturated and unsaturated mid-blocks), functionalized polyolefins (ethylene or propene copolymers with oxygen containing monomers), or APAOs (ethylene-, propene-, or butene copolymers), and EVA (ethylene vinyl acetate).

SUMMARY OF THE INVENTION

The invention provides hot melt adhesive formulations, preferably composed of an ethylene vinyl acetate copolymer (EVA), tackifying resin, a hydrogenated styrenic block copolymer (HSBC) and a liquid plasticizer. These formulations provide superior hot tack, adhesion characteristics, resistance to blocking and/or cold flow, and fast set speed over traditional EVA, APAO and SBC adhesives. Applications include, but are not limited to, disposable gowns, diapers, sanitary pads, general assembly, and filtration.

Accordingly, in one aspect, there is provided a hot melt adhesive composition comprising;
 (a) about 5% to 40% by weight of an ethylene vinyl acetate polymer;
 (b) about 30% to 70% by weight of a tackifying resin;
 (c) about 2% to 30% by weight of a hydrogenated styrenic block copolymer; and
 (d) about 2% to 40% by weight of a liquid plasticizer.

In yet another aspect, the ethylene vinyl acetate polymer is a copolymer of ethylene and vinyl acetate, with a vinyl acetate content of between about 8 and about 28 percent by weight. More preferably the vinyl acetate content is between about 8 and about 18 percent. The ethylene vinyl acetate copolymer preferably has a melt index greater than about 2 g/10 minutes and more preferably greater than about 5 g/10 minutes. The ethylene vinyl acetate copolymer is more preferably present in the range of about 5% to about 35% by weight, and is most preferably present in the range of about 10% to about 28% by weight of the finished adhesive.

In still another aspect, the tackifying resin is selected from aliphatic and cyclo-aliphatic petroleum hydrocarbon resins, hydrogenated aliphatic and cyclo-aliphatic petroleum hydrocarbon resins, hydrogenated aromatic petroleum hydrocarbon resins, aliphatic/aromatic petroleum derived hydrocarbon resins, hydrogenated aliphatic/aromatic derived hydrocarbon resins, aromatic modified cyclo-aliphatic resins, hydrogenated aromatic modified cyclo-aliphatic resins, polyterpene resins, copolymers and terpolymers of natural terpenes, and mixtures thereof. Preferably, the tackifying resin has a softening point equal to or greater than about 90° C., and is present in the range of about 30% to about 70% by weight.

In still another aspect, the hydrogenated styrenic block copolymer is present in an amount of from about 2% to about 30% by weight, preferably from about 5% to about 25% by weight, and most preferably from about 7% to about 20% by weight. The hydrogenated SBC is selected from the group comprising styrene-ethylene-butylene-styrene (SEBS), styrene-ethylene-butylene (SEB), styrene-ethylene-propylene-styrene (SEPS), styrene-ethylene-propylene (SEP) and styrene-ethylene-ethylene-propylene-styrene (SEEPS). Preferably, the hydrogenated styrenic block copolymer is an SEBS, SEPS or SEEPS polymer. Also, its styrene content is preferably about 20% to about 35% by weight, more preferably about 25% to about 35% by weight. Most preferably, the styrenic block copolymer is an SEBS having a styrene content of about 30% by weight. If diblock is present in the polymer, it should be kept to less than about 30% by weight. Preferably, the polymer contains substantially no diblock.

In still another aspect, the plasticizer is a liquid mineral oil.

As the adhesive composition of the present invention will typically be used in spray applications, its Brookfield viscosity (ASTM D3236) measured at 325° F. should be 20,000 centipoise (cP) or less, preferably 15,000 cP or less, and most preferably 10,000 cP or less.

DETAILED DESCRIPTION OF THE INVENTION

It has been discovered that a combination of an ethylene vinyl acetate copolymer, a tackifier, a hydrogenated styrenic block copolymer, and a liquid plasticizer can be incorporated into hot melt adhesive formulas that will exhibit a fast set speed, improved hot tack and increased adhesion characteristics, while resisting blocking and cold flow.

Ethylene vinyl acetate copolymers have been widely used in hot melt adhesives for many years. There is a wide product range of these materials and are available from several different suppliers, including ExxonMobil Chemicals, DuPont Co., Celenese Corporation and Westlake Chemical.

EVA copolymers can range from about 2% vinyl acetate to over 40% by weight. The grades used in hot melt adhesives typically contain about 8% to about 40% vinyl acetate by weight. They also vary widely in molecular weight which is reflected in the melt index of the polymer. Grades of EVA are available with melt indexes of less than 1 to greater than 1000 grams/10 minutes. Melt Index is determined according to ASTM D1238 using a 2.16 kilogram weight and a test temperature of 190° C.

The disposable nonwoven article industry is one of the biggest users of hot melt adhesives. While EVA copolymers have been used for decades in hot melt adhesives, they are not used to a significant degree in manufacturing nonwoven disposable articles. Instead, hot melt pressure sensitive adhesives based on styrenic block copolymers represent the vast majority of the adhesives used to construct nonwoven articles. The majority of the application equipment used today to bond these articles together is hot melt spray technology. This began in the 1980's and became the preferred method soon thereafter. Spray technology can deliver the adhesive to the substrate without any direct contact of the hot application head to the substrate. This is important since the vast majority of the articles made use very thin polyethylene films as backsheets in manufacturing disposable diapers, adult incontinence products and various feminine care products. Although the hot melt exits the spray nozzle at a relatively high temperature (as high as 350° F.), it cools rapidly as it is transported to the substrate. In addition, it is applied over a wider area than a typical bead application. All of these factors help to minimize the thermal shock to the thin polyethylene substrate. If the adhesive is too hot when it contacts the film, distortion, melting, or pinholes of the film can occur. This can lead to the substrate tearing or leakage of the article. Today, spray application is the dominant method of applying hot melts for nonwoven disposable articles. There are many manufacturers of this type of equipment, including Nordson Corporation and ITW Dynatec.

EVA copolymers are commodity materials and tend to be fairly low in price compared to many other polymers used to manufacture hot melt adhesives. They also have excellent adhesion characteristics because of the polarity of the vinyl acetate functionality. Unfortunately, these copolymers do not spray well using typical hot melt spray equipment. They lack the strength and elasticity to spray well using conventional equipment. Therefore, a need exists to find a way to modify these polymers so that they can be sprayed using typical hot melt spray equipment.

Previous attempts to add various modifiers to EVA copolymers to increase their sprayability have not been successful. It has been very difficult to find a blend of polymers with the right balance of viscosity, open time, adhesion, etc. along with the necessary degree of compatibility.

We have found a novel combination of ethylene vinyl acetate copolymers blended with certain hydrogenated block copolymers that gives a hot melt adhesive with excellent performance characteristics along with very good sprayability. This combination of properties has not been achieved before. These products can also be tailored to exhibit very low bleed through and blocking characteristics.

There are many different types of styrenic block copolymers available today in the marketplace. They are available in a number of different chemical types and structure types. Examples of the block copolymers conventionally used in hot melt adhesive compositions are styrenic block copolymers (SBC) and include styrene-butadiene (SB), styrene-butadiene-styrene (SBS), styrene-isoprene-styrene (SIS), styrene-isoprene (SI), styrene-isoprene-butadiene-styrene (SIBS), styrene-ethylene-butylene-styrene (SEBS), styrene-ethylene-butylene (SEB), styrene-ethylene-propylene-styrene (SEPS), styrene-ethylene propylene (SEP) and styrene-ethylene-ethylene-propylene-styrene (SEEPS or hydrogenated SIBS).

Useful elastomeric block copolymers used in hot melts are those having structures such as A-B, A-B-A, A-(B-A)$_n$-B, or (A-B)$_n$-Y wherein A comprises a polyvinyl aromatic block having a Tg higher than 80° C., B comprises a rubbery midblock having a Tg lower than −10° C., Y comprises a multivalent compound, and n is an integer of at least 3.

For purposes of the present invention, it is important that the styrenic block copolymer be hydrogenated. Preferred polymers are styrene-ethylene-butylene-styrene (SEBS), styrene-ethylene-butylene (SEB) styrene-ethylene-propylene-styrene (SEPS) and styrene-ethylene-propylene (SEP) and styrene-ethylene-ethylene-propylene-styrene (SEEPS or hydrogenated SIBS). Particularly preferred polymers are the SEBS and SEEPS grades.

Within the range of SEBS polymers, we have found that those with about 30% styrene have good compatibility with the EVA polymer. Particularly preferred is Kraton G1652, which is manufactured by Kraton Performance Polymers. This polymer has a styrene content of 30%, a Melt Index (ASTM D1238, 5 kg. 230° C.) of 5 grams/10 minutes, and a diblock content of 0 percent.

The second polymer used in the adhesive is an ethylene vinyl acetate copolymer with a vinyl acetate content of between 8 and 28 percent by weight, and more preferably between 8 and 18% by weight. The ethylene vinyl acetate copolymer has a melt index greater than 2 g/10 minutes and more preferably greater than 5 g/10 minutes. The ethylene vinyl acetate copolymer is more preferably present in the range of about 5% to about 35% by weight, and is most preferably present in the range of about 10% to about 28% by weight of the adhesive.

It is conceivable that other polymers similar to EVA in polarity may be used to replace part or all of the EVA in the formula. For example, ethylene methyl acrylate, ethylene ethyl acrylate, ethylene butyl acrylate, ethylene methacrylic acid, ethylene methyl methacrylate, etc may be used providing it has the desired compatibility with the hydrogenated styrenic block copolymer.

The adhesives of the invention contain a tackifying resin in combination with ethylene vinyl acetate copolymer, hydrogenated styrenic block copolymer and the liquid plasticizer. The tackifying resins are selected for a specific degree of compatibility with the polymers and plasticizer.

Representative resins include the $C_5/C_9$ hydrocarbon resins, synthetic polyterpenes, rosin, rosin esters, natural terpenes, and the like. More particularly, the useful tackifying resins include any compatible resins or mixtures thereof such as (1) natural and modified rosins including gum rosin, wood rosin, tall oil rosin, distilled rosin, hydrogenated rosin, dimerized rosin, and polymerized rosin; (2) glycerol and pentaerythritol esters of natural and modified rosins, including the glycerol ester of pale, wood rosin, the glycerol ester of hydrogenated rosin, the glycerol ester of polymerized rosin, the pentaerythritol ester of hydrogenated rosin, and the phenolic-modified pentaerythritol ester of rosin; (3) copolymers and terpolymers of natural terpenes, such as styrene/terpene and alpha methyl styrene/terpene; (4) polyterpene resins generally resulting from the polymerization of terepene hydrocarbons, such as the bicyclic monoterpene known as pinene, in the presence of Friedel-Crafts catalysts at moderately low temperatures; also included are the hydrogenated polyterpene resins; (5) phenolic modified terpene resins and hydrogenated derivatives thereof such, for example, as the resin product resulting from the condensation, in an acidic medium, of a bicyclic terpene and a phenol; (6) aliphatic petroleum hydrocarbon resins resulting from the polymerization of monomers consisting primarily of olefins and diolefins; also included are the hydrogenated aliphatic petroleum hydrocarbon resins; and (7) cyclic petroleum hydrocarbon resins and the hydrogenated derivatives thereof. Mixtures of two or more of the above described tackifying resins may be required for some formulations. Also included are the cyclic or acylic $C_5$ resins and aromatic modified acyclic or cyclic resins.

The tackifying resin should have a Ring and Ball softening point (measured by ASTM E28) of at least about 90° C., and preferably between about 95° C. and about 140° C., and most preferably the softening point is between about 95° C. and about 130° C. A preferred tackifier is a hydrogenated aromatic modified dicyclopentadiene resin with a Ring and Ball softening point between about 100° C. to 130° C., such as Escorez 5600 or Escorez 5615. Other preferred tackifying resins are fully hydrogenated resins regardless of type like aliphatic or cycloaliphatic hydrocarbon resins such as, Eastotac® H100W, or Sukorez® SU210, a pure aromatic monomer resin such as Regalrez 1126, and DCPD (dicyclopentadiene) resins with no aromatic content such as Escorez 5400.

Other preferred tackifying resins are partially hydrogenated aliphatic hydrocarbon resins such as Eastotac H100L and Eastotac H100R, as well as non-hydrogenated aliphatic C5 resins and aromatic modified C5 resins with low aromaticity such as Piccotac 1095 and Piccotac 9095, respectively.

The tackifiers are generally present in the adhesive compositions in an amount greater than the combined amount of the HSBC and EVA polymers. Within this range, amounts of about 30 to 70% by weight of the composition, preferably about 40 to 65% by weight are utilized, and most preferably about 45 to 60% by weight. Blends of two or more tackifying resins may also be used. For example, a blend of a first tackifying resin and a second tackifying resin that is different than the first tackifying resin may also be employed. From about 0% to about 65% by weight of one or more additional tackifying resins may be blended together with the first tackifying resin if desired.

Hot melt adhesive formulas according to the present invention also contain about 2% to about 40%, preferably about 5% to about 35%, and more preferably about 10% to about 30%, by weight, of any plasticizer. A plasticizer is broadly defined as a typically organic composition that can be added to rubbers and other resins to improve extrudability, flexibility, workability, or stretchability. A suitable plasticizer may be selected from the group which not only includes the usual plasticizing oils, such as mineral oil, but also olefin oligomers and low molecular weight polymers, glycol benzoates, as well as vegetable and animal oil and derivatives of such oils. The petroleum-derived oils that may be employed are relatively high boiling temperature materials containing only a minor proportion of aromatic hydrocarbons. In this regard, the aromatic hydrocarbons should preferably be less than 30%, and more particularly less than 15%, by weight, of the oil. Alternately, the oil may be totally non-aromatic. The oligomers may be polypropylenes, polybutenes, hydrogenated polyisoprene, hydrogenated butadiene, or the like having average molecular weights between about 100 and about 10,000 g/mol. Suitable vegetable and animal oils include glycerol esters of the usual fatty acids and polymerization products thereof. Other plasticizers may be used provided they have suitable compatibility. Nyflex 222B, a naphthenic mineral oil manufactured by Nynas Corporation, has also been found to be an appropriate plasticizer. As will be appreciated, plasticizers have typically been employed to lower the viscosity of the overall adhesive composition without substantially decreasing the adhesive strength and/or the service temperature of the adhesive. The choice of plasticizer can be useful in formulation for specific end uses (such as wet strength core applications). Because of economics involved in production and in material cost, as plasticizers are usually of lower cost than other materials involved in the formulation like polymers and tackifying resins, the amount of plasticizer in the adhesive should be maximized for cost considerations.

Hot melts of the present invention may also contain relatively small amounts of other auxiliary agents such as plasticizing oils, waxes or other additives as long as they don't detract from the performance of the adhesive. If they are present, the amount of such auxiliary agents will generally be below 10 percent by weight.

Waxes can be used as an auxiliary agent in the adhesive composition, and are used to reduce the melt viscosity of the hot melt construction adhesives without appreciably decreasing their adhesive bonding characteristics. These waxes also are used to reduce the open time of the composition without affecting the temperature performance.

The wax material component of the adhesive is optional but when included may comprise up to about 10% by weight, preferably only up to 5% by weight, of the adhesive composition.

Among the useful wax materials are:

(1) Low molecular weight, that is, 100-6000 g/mol, polyethylene having a hardness value, as determined by ASTM method D-1321, of from about 0.1 to 120 and ASTM softening points of from about 66° C.° to 120° C.;

(2) Petroleum waxes such as paraffin wax having a softening point of from about 130° to 170° F. and microcrystalline wax having a softening point of from about 135° to 200° F., the latter softening points being determined by ASTM method D127-60;

(3) metallocene catalyzed propylene-based wax like those commercialized by Clariant under the name "Licocene".

(4) metallocene catalyzed wax or single-site catalyzed wax like for example those described in U.S. Pat. Nos. 4,914,253, 6,319,979 or WO 97/33921 or WO 98/03603.

(5) synthetic waxes made by polymerizing carbon monoxide and hydrogen such as Fischer-Tropsch wax; and (6) polyolefin waxes. As used herein, the term "polyolefin wax" refers to those polymeric or long-chain entities comprised of olefinic monomer units. These materials are commercially available from Eastman Chemical Co. under the trade name "Epolene." The materials which are preferred to use in the compositions of the present invention have a Ring and Ball softening point of 200° F. (93° C.) to 350° F. (177° C.).

As should be understood, each of these waxes is solid at room temperature. Other useful substances include hydrogenated animal, fish and vegetable fats and oils such as hydrogenated tallow, lard, soy oil, cottonseed oil, castor oil, etc., and which are solid at ambient temperature by virtue of their being hydrogenated, have also been found to be useful with respect to functioning as a wax material equivalent. These hydrogenated materials are often referred to in the adhesives industry as "animal or vegetable waxes".

The adhesive also typically includes a stabilizer or antioxidant. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final product to the ambient environment. Such degradation is usually manifested by deterioration in the appearance, physical properties and performance characteristics of the adhesive. A particularly preferred antioxidant is Irganox 1010, a tetrakis(methylene (3,5-di-tert-butyl-4-hydroxyhydrocinnamate))methane manufactured by BASF among others.

The adhesive composition useful in the method of the present invention may be produced using any of the techniques known in the art. A representative example of the procedure involves placing all of the liquid substances in a jacketed mixing kettle and preferably in a jacketed heavy duty mixer of the Baker-Perkins or Day type, and which is equipped with rotors, and thereafter raising the temperature of this mixture to a range of 120° C. to 177° C. The solid tackifying resins and other additives are then added and melted to form a homogeneous mixture. Finally, the polymer is added and mixed until completely blended in. It should be understood that the precise temperature to be used in this step would depend on the melting point of the particular ingredients and the viscosity of the finished adhesive. The resulting adhesive composition is agitated until the polymers completely dissolve. A vacuum is then applied to remove any entrapped air.

The following materials were used:

Piccotac 9095 is a aromatic modified hydrocarbon resin with a 95° C. softening point. It can be obtained from Eastman Chemical Co.

Eastotac™ H-142R is a hydrogenated hydrocarbon resin, having a Ring and Ball softening point of 142° C. and a molten Gardner color of 4. It is available from Eastman Chemical Company.

Escorez 5637 is a hydrogenated aromatic modified cycloaliphatic hydrocarbon resin with a 130° C. softening point. It is available from ExxonMobil Chemical.

Quintone DX390N is a C5/C9 resin with a 100° C. softening point available from Zeon Chemical.

Kraton 1652 is a hydrogenated styrene-ethylene/butylene block copolymer containing 30 percent styrene and essentially zero percent diblock. It has a melt index of 5 grams/10 minutes using ASTM D1238 with a 5 kilogram weight and a test temperature of 230° C. It is available from Kraton Performance Polymers.

Escorene UL7510 is an ethylene/vinyl acetate copolymer made by ExxonMobil Chemical Co. It has a vinyl acetate content of 18.7% percent and a melt flow rate of 500 grams/10 minutes using ASTM D-1238 at 190° C./2.16 kg.

EF 532 is an ethylene/vinyl acetate copolymer made by Westlake Chemical Co. It has a vinyl acetate content of 12% percent and a melt flow rate of 8 grams/10 minutes using ASTM D-1238 at 190° C./2.16 kg.

Escorene UL7560 is an ethylene/vinyl acetate copolymer made by ExxonMobil Chemical Co. It has a vinyl acetate content of 18.7% percent and a melt flow rate of 2.1 grams/10 minutes using ASTM D-1238 at 190° C./2.16 kg.

Escorene UL7750 is an ethylene/vinyl acetate copolymer made by ExxonMobil Chemical Co. It has a vinyl acetate content of 27.6% percent and a melt flow rate of 25 grams/10 minutes using ASTM D-1238 at 190° C./2.16 kg.

RGG is a hydrogenated beef tallow with a Ring & Ball Softening Point of about 140° F. It is available from the Seydel Company, Inc.

Irganox 1010 is a hindered phenolic antioxidant. It is available from Ciba Specialty Chemicals.

Nyflex 222B is a hydrotreated napthenic process oil available from Nynas Corporation.

The following tests were performed on the adhesives to determine the viscosity, softening point and peel strength.

The resulting hot melt adhesives may be then applied to substrates using a variety of application techniques. Examples include hot melt glue gun, hot melt slot-die coating, hot melt wheel coating, hot melt roller coating, melt blown coating, spiral spray and the like. In a preferred embodiment, the hot melt adhesive is sprayed onto a substrate using spiral spray, which is a preferred technique to produce a filamentary spiral pattern for elastic attachment and construction in diaper manufacturing. In one example, a hot melt coater is equipped with a disc like coating die which has a nozzle tip in the center. The tip is surrounded with a series of inclined orifices for hot air jets to pass through. The hot melt adhesive is pumped out of the nozzle in the form of a fine filament. The filament is then rotated by high-velocity hot air jets coming out of the orifices, thereby producing a helical pattern from a single strand of adhesive which is transported to the substrate. It is not the intent of this invention to provide a full description of spray techniques and the details can be found in the literature.

For the present invention, preferred methods of applying the adhesive would be by spray application, most preferably assisted by air. Among these techniques, the most common are spiral spray (Controlled Fiberization™ by Nordson), Summit™ by Nordson, Surewrap™ by Nordson, Omega™ by ITW and various melt blown processes. For the present invention, the temperature at which the hot melt adhesive is applied should be below 170° C., so that the heat sensitive substrates will not be damaged. Preferably, this temperature should be equal to or lower than 160° C., most preferably lower than 150° C.

The adhesive composition of the present invention may be used in a number of applications such as, for example, in disposable nonwoven hygienic articles, paper converting, flexible packaging, wood working, carton and case sealing, labeling and other assembly applications. Particularly preferred applications include disposable diaper and feminine sanitary napkin construction, adult incontinent brief construction attachment, diaper and napkin core stabilization, diaper backsheet lamination, industrial filter material conversion, surgical gown and surgical drape assembly, etc. The adhesives of the present invention are particularly suited as a construction adhesive for use on disposable diapers, training pants and adult incontinent products. Since the hot melt adhesive can be formulated to have no pressure sensitivity at room temperature, they are particularly useful when applied on very open substrates such as low basis weight nonwoven fabrics or apertured polyethylene.

Instrumental Characterization

Brookfield viscosity was tested according to ASTM D-3236 Method at 350° F. (177° C.), and are reported in centipoise (cP units).

Dynamic Temperature Testing

The rheology of a given hot melt adhesive can be determined using a TA Instruments rheometer, such as an Ares 3 model. For the adhesives listed in the tables below, a temperature step procedure was used to determine the storage modulus G' and loss modulus G" at various temperatures as well as the cross-over temperature $T_x$ and the glass transition temperature $T_g$, and can be measured as is conventional in this art according to ASTM D-4440-01. The instrument was set to a frequency of 10 radians per second and the temperature was varied from +140° C. to −40° C. The parallel plates used had a 25 mm diameter and a 1.6 millimeter gap.

In general, hot melt adhesives such as those described in this application, become non-tacky when the storage modulus (G') at 25° C. is greater than about $1 \times 10^6$ dynes/cm². For this reason, when the adhesive is used on a relatively open substrate, such as low basis weight nonwovens or apertured polyethylene film where bleed-through or blocking might be a concern, the G' should be greater than $1.0 \times 10^6$ dynes/cm² at 25° C. Most conventional hot melt pressure sensitive adhesives used in diaper and fem care pad construction have a G' of less than $1.0 \times 10^6$ dynes/cm² or even less than $5.0 \times 10^6$ dynes/cm². This can lead to the diaper or pad sticking to itself or to other packaging material. Even worse is tearing of the article as it is being removed from the packaging material before use. This can render the product unusable or make it prone to leakage.

Rheological analysis of the novel adhesive formulations described in this invention show a rapid increase in G' (storage modulus) between 30° C. and 70° C. This rapid increase in G' is characteristic of fast set speed. This increase in modulus is greater than 2 orders of magnitude.

Performance Evaluation

Bond evaluations of the novel adhesive formulations described in this invention show superior performance over traditional EVA, APAO and SBC adhesives. Peel values using the novel adhesive formulations described in this invention show increases in strength. This increase in peel strength does not come at the expense of increased blocking and/or cold flow as is seen with traditionally formulated EVA, APAO and SBC adhesives Peel strength retention at elevated temperatures of the novel adhesive formulations described in this invention are greatly increased as compared to traditionally formulated EVA, APAO and SBC adhesives.

The invention provides a hot melt adhesive composition, comprising a blend of the following components for use in a polypropylene nonwoven substrate lamination application. Table One shows several formulations comprising a blend of ethylene vinyl acetate copolymers and an SEBS block copolymer, tackifying resin and mineral oil. Physical properties and selected rheology data are also shown. The abbreviation "Vis" refers to viscosity reported in centipoise (cP), and was determined in accordance with ASTM D-3236 at 350° F. (177° C.). G' refers to storage modulus reported in dynes/cm² at 25° C., and was determined in accordance with the rheology testing procedure described herein. $T_x$ refers to cross-over temperature reported in degrees Centigrade (° C.), and is the temperature at which storage modulus G' equals loss modulus G". $T_g$ refers to glass transition temperature reported in degrees Centigrade (° C.), and was determined in accordance with the rheology testing procedure described herein. The ASTM procedures for rheology testing, which includes obtaining the cross-over temperature $T_x$, the storage modulus G', the loss modulus G" and the glass transition temperature $T_g$, are all contained in ASTM D-4440-01. Ring and Ball softening point (R&B SP) is reported in ° F. or ° C., and was determined in accordance with ASTM E-28.

TABLE ONE

| | Ex. 1 | Ex. 2 | Ex. 3 | Ex. 4 | Ex. 5 | Ex. 6 | Ex. 7 |
|---|---|---|---|---|---|---|---|
| Raw Material | | | | | | | |
| Piccotac 9095 | 45.0 | 58.2 | 42.1 | 56.1 | 59.9 | 38.8 | |
| Eastotac H-142R | | | 13.0 | | | | |
| Escorez 5637 | | | | | | 13.0 | |
| Quintone DX390 | | | | | | | 55.0 |
| Kraton G1652 | 9.2 | 13.4 | 9.1 | 11.8 | 13.5 | 17.4 | 9.2 |
| Escorene UL 7510 | 22.7 | 8.5 | | 7.8 | | 14.4 | |
| EF532AA | | 3.5 | | | 3.5 | | |
| Escorene UL 7560 | | | 7.8 | | 2.6 | | |
| Escorene UL7750 | | | | | | | 9.2 |
| RGG | | 1.8 | | | | | |
| Nyflex 222B | 22.5 | 14.0 | 27.4 | 23.7 | 19.9 | 15.8 | 26.5 |
| Irganox 1010 | 0.1 | 0.1 | 0.1 | 0.1 | 0.1 | 0.1 | 0.1 |
| TOTAL | 100.0 | 100.0 | 100.0 | 100.0 | 100.0 | 100.0 | 100.0 |

TABLE ONE-continued

|  | Ex. 1 | Ex. 2 | Ex. 3 | Ex. 4 | Ex. 5 | Ex. 6 | Ex. 7 |
|---|---|---|---|---|---|---|---|
| PHYSICAL PROPERTIES | | | | | | | |
| Vis at 350° F. (cP) | 900 | 1575 | 775 | 525 | 1375 | 2525 | 625 |
| Vis at 325° F. (cP) | 1350 | 2550 | 1225 | 850 | 2275 | 4525 | 975 |
| Vis at 300° F. (cP) | 2250 | 4950 | 2025 | 1425 | 4315 | 8600 | 1625 |
| Vis at 275° F. (cP) | 3750 | 11050 | 3650 | 2775 | 9750 | 16950 | 2925 |
| Vis at 250° F. (cP) | 6550 | 29000 | 7275 | 710 | 27000 | 40500 | 5950 |
| R&B SP (° F.) | 175 | 195 | 172 | 186 | 200 | 218 | 168 |
| RHEOLOGY | | | | | | | |
| Tx (° C.) | 50.2 | 57.2 | 67.0 | 85.0 | 90.0 | 94.1 | Not run |
| G' at 25° C. (dynes/cm) | $2.3 \times 10^6$ | $1.4 \times 10^7$ | $1.1 \times 10^6$ | $1.5 \times 10^6$ | $3.2 \times 10^6$ | $8.0 \times 10^6$ | Not run |
| Tg (° C.) | 12.6 | 29.8 | 17.0 | 20.0 | 15.0 | 26.4 | Not run |

All of the mixes shown in Table One showed excellent compatibility with no phase separation during heat aging. They were also clear when molten which indicates good compatibility.

In Table Two, two prior art products are shown along with their physical properties. H9564 is an olefin based hot melt which is used as diaper construction product. H20080 is also a disposable diaper construction product, but is based on a non-hydrogenated styrenic block copolymer. Neither of these products contain any EVA. They are both commercially available from Bostik, Inc.

TABLE TWO

|  | H9564 | H20080 |
|---|---|---|
| PHYSICAL PROPERTIES | | |
| Vis at 350° F. (cP) | Not run | 1200 |
| Vis at 325° F. (cP) | 1530 | 2100 |
| Vis at 300° F. (cP) | 2470 | 3140 |
| Vis at 275° F. (cP) | 4220 | 7025 |
| Vis at 250° F. (cP) | 7800 | |
| R&B SP (° F.) | 194 | 175 |
| RHEOLOGY | | |
| Tx (° C.) | None | 80.9 |
| G' at 25° C. (dynes/cm²) | $1.2 \times 10^6$ | $3.2 \times 10^6$ |
| Tg (° C.) | 23.6 | 18.6 |

Performance

In order to determine the adhesive peel performance, sample laminates of a 15 grams per square meter (15 g/m² or 15 GSM) spunbond nonwoven top sheet from First Quality Nonwovens were adhered to a breathable polyethylene using a Nordson Signature™ spray head and a two inch wide adhesive pattern. The laminates were allowed to age for 24 hours before being pulled apart by an Instron tensile tester at a rate of 12 inches per minute in a climate controlled room, which is maintained at a constant 75° F. and 50% relative humidity. The peel force was measured in grams and the peel value was calculated by determining the average peel strength after eliminating the first and last five percent of the sample length to reduce variability from starting and stopping the test. This test was performed using two different add-on levels, 2.0 grams per square meter and 4.2 grams per square meter. The adhesive was applied at a temperature of 149° C. (300° F.) and the open time was 0.12 seconds. The peel force for each of the prior art adhesives as well as Examples 1 and 3-5 are shown in Table Three. The peel force value is given in grams per inch width.

TABLE THREE

| Product | Ex. 1 | Ex. 2 | Ex. 3 | Ex. 4 | Ex. 5 | Ex. 6 | Ex. 7 | H9564 | H20080 |
|---|---|---|---|---|---|---|---|---|---|
| 2.0 GSM Add-on | 70 g | Not run | 69 g | 58 g | 53 g | Not run | Not run | 85 g | 98 g |
| 4.2 GSM Add-on | 160 g | Not run | 212 g | 170 g | 192 g | Not run | Not run | 238 g | 232 g |

Blocking Tests

Several of the adhesive samples were evaluated for their resistance to blocking In this test, a sample of the laminate as prepared above at an add-on level of 4.2 GSM, is placed against another layer of nonwoven so that the nonwoven layer of the laminate is in direct contact with the second nonwoven. This mimics what happens when the diaper is in the package. A weight equal to 200 grams per square centimeter is placed on top of the construction and is place in an incubator over at 60° C. (140° F.) for 48 hours. After that time, the sample is removed from the oven and allowed to cool to room temperature. The average peel force needed to separate the two nonwoven layers is determined using an Instron tensile tester with a crosshead speed of 12 inches per minute.

A typical styrenic block copolymer based construction product, H20080, exhibited a blocking test value of 112 grams per inch wide pattern in this test. This is an unacceptably high value, which would likely result in tearing of the substrates upon opening the diaper. For this test, it is desirable to have as low a peel force as possible. Typically a force of less than 50 grams per inch wide sample is desired. More preferred is less than 25 grams per inch. H9564 is an olefin based diaper construction adhesive and gave a value of 26 grams per inch, which is a borderline value.

The blocking force is highly dependent on the basis weight of the nonwoven. The lower the basis weight, the higher the blocking value will be since the fabric has more open spaces where the adhesive is exposed.

A second more severe blocking test was performed using two different basis weight nonwovens. The nonwoven substrates were spunbond fabrics with basis weights of 18 GSM and 10 GSM. First, polyethylene to nonwoven laminates were prepared as described above, but the adhesive add-on rate was increased to 7 grams per square meter, which is considered high for a construction application. For many diaper applications, a 10 GSM nonwoven is considered fairly low, so the combination of a 10 GSM nonwoven with a 7 GSM adhesive add-on is a very difficult combination.

Examples 1 and 2 from Table 1 were evaluated in this test. Example 1 gave a blocking value of 8 grams per inch with the 18 GSM nonwoven and 20 grams/inch with the 10 GSM nonwoven. Example 2 gave values of 8 grams/inch and 15 grams/inch for the 18 and 10 GSM nonwovens respectively.

The invention claimed is:

1. A hot melt adhesive composition, consisting of:
   about 5% to about 40% by weight of an ethylene vinyl acetate copolymer having a melt index greater than about 2 g/10 minutes;
   about 30% to about 70% by weight of a tackifying resin;
   about 7% to about 17.4% by weight of a hydrogenated styrenic block copolymer comprising a styrene-ethylene-butylene-styrene polymer and having a diblock content of less than about 30% by weight relative to the weight of the hydrogenated styrenic block copolymer;
   about 14% to about 40% by weight of a liquid plasticizer selected from the group consisting of mineral oil, polybutene, or mixtures thereof; and
   about 0% to about 5% by weight of a stabilizer;
   wherein the viscosity of the composition is equal to or less than about 20,000 centipoise at 325° F.

2. The composition of claim 1 wherein the composition has a storage modulus at 25° C. that is greater than about $1\times10^6$ dynes/cm$^2$.

3. The composition of claim 1 comprising about 10% to about 28% by weight of said ethylene vinyl acetate copolymer.

4. The composition of claim 1 comprising about 14% to about 30% by weight of said liquid plasticizer.

5. The composition of claim 1 wherein said composition has a viscosity equal to or less than 15,000 centipoise at 325° F.

6. The composition of claim 1 wherein said composition has a viscosity equal to or less than 10,000 centipoise at 325° F.

7. The composition of claim 1 wherein said hydrogenated styrenic block copolymer has a styrene content of about 25% to about 35% by weight.

8. The composition of claim 1 wherein said hydrogenated styrenic block copolymer has no diblock content.

9. The composition of claim 1 wherein the tackifying resin has a softening point equal to or greater than about 90° C.

10. The composition of claim 1 wherein the tackifying resin has a softening point of from about 95° C. to about 140° C.

11. The composition of claim 1 wherein the tackifying resin has a softening point of from about 95° C. to about 130° C.

12. The composition of claim 1 having about 40% to about 65% by weight of said tackifying resin.

13. The composition of claim 1 having about 45% to about 60% by weight of said tackifying resin.

14. The composition of claim 1 wherein the vinyl acetate content of said ethylene vinyl acetate copolymer is about 8% to about 28% by weight based on the ethylene vinyl acetate copolymer.

15. The composition of claim 1 wherein the vinyl acetate content of said ethylene vinyl acetate copolymer is about 8% to about 18% by weight based on the ethylene vinyl acetate copolymer.

16. A laminate comprising a first layer of nonwoven material and a second layer of nonwoven material, bonded together with the adhesive composition of claim 1.

17. A laminate comprising a first layer of nonwoven material and a second layer of film material, bonded together with the adhesive composition of claim 1.

18. The laminate of claim 17 wherein said film comprises a polyethylene film, a polypropylene film, an ethylene-propylene copolymer film or a cloth-like coated film material.

19. An article comprising the adhesive composition of claim 1.

20. The article of claim 19 comprising a disposable diaper, a sanitary napkin, a bed pad, a bandage, a surgical drape, a tape, a label, a plastic sheet, a nonwoven sheet, a paper sheet, a cardboard, a book, a filter, or a package.

21. The composition of claim 1, wherein said hydrogenated styrenic block copolymer consists of the styrene-ethylene-butylene-styrene polymer.

22. The composition of claim 1, wherein the ethylene vinyl acetate copolymer has a melt index greater than about 5 g/10 minutes.

23. The composition of claim 1, wherein the ethylene vinyl acetate copolymer has a melt index no more than about 500 g/10 minutes.

* * * * *